(12) United States Patent
Wagner et al.

(10) Patent No.: US 6,875,612 B2
(45) Date of Patent: Apr. 5, 2005

(54) MONOCYTE-SPECIFIC PARTICULATE DELIVERY VEHICLE

(75) Inventors: Thomas E. Wagner, Greenville, SC (US); Xianzhang Yu, Mauldin, SC (US)

(73) Assignee: Greenville Hospital System, Greenville, SC (US)

( * ) Notice: Subject to any disclaimer, the term of this patent is extended or adjusted under 35 U.S.C. 154(b) by 34 days.

(21) Appl. No.: 10/112,036

(22) Filed: Apr. 1, 2002

(65) Prior Publication Data

US 2002/0155609 A1 Oct. 24, 2002

Related U.S. Application Data

(60) Provisional application No. 60/279,769, filed on Mar. 30, 2001.

(51) Int. Cl.[7] .................. C12N 15/87; C12N 15/00; C12N 5/00; C12P 21/06; A61K 39/23
(52) U.S. Cl. .............. 435/459; 435/69.1; 435/69.3; 435/320.1; 435/455; 435/456; 435/325; 424/204.1; 424/233.1
(58) Field of Search .................. 435/69.1, 325, 435/91.41, 91.42, 455, 456, 235.1, 459, 69.3, 320.1, 366, 462, 457; 424/233.1

(56) References Cited

U.S. PATENT DOCUMENTS

| | | |
|---|---|---|
| 6,630,169 B1 * 10/2003 | Bot et al. | 424/489 |
| 2002/0006412 A1 * 1/2002 | Roberts et al. | 424/233.1 |

FOREIGN PATENT DOCUMENTS

| | | | |
|---|---|---|---|
| EP | 0 535 576 A1 | 4/1993 | |
| WO | WO 97 11605 A1 | 4/1997 | |
| WO | WO 00 60054 A1 | 10/2000 | |
| WO | WO 00/60054 | * 10/2000 | C12N/5/10 |

OTHER PUBLICATIONS

Hammond et al. A Particulate Viral Protein Vaccine Reduces Viral Load and Delays Progression to Disease in Immunized Ponies Challenged with Equine Infectious Anemia Virus. Virology 254, 37–49 (1999).*
Furth. Gene Transfer by Biolistic Process. Molecular Biotechnology. 7, 139–143 (1997).*
Jacqueline Guy et al., "Delivery of DNA into mammalian cells by receptor–mediated endocyutosis and gene therapy." *Molecular Biotechnology*, 1995. 3(3):236–248. Biosciences Information Service, Philadelphia, PA. DATABASE Biosis Online! (XP002206227).
T. Ragot et al., "Replication–defective recombinant adenovirus expressing the Epstein–Barr virus (EBV) envelope glycoprotein gp340/220 induces protective immunity against EBV–induced Lymphomas in the cottontop tamarin." *J. of General Virology*, 1993, 74(3):501–507. Biosciences Information Service, Philadelphia, PA. DATABASE Biosis Online! (XP002206228).
Martine Monteil et al., "Single inoculation of replication–defective adenovirus–vectored vaccines at birth in piglets with maternal antibodies induces high level of antibodies and protection against pseudorabies." *Vaccine*, 2000, 18(17):1738–1742. Biosciences Information Service, Philadelphia, PA. DATABASE Biosis Online! (XP002206229).
Torao Tanaka et al., "Andenovirus–mediated prodrug gene therapy for carcinoembryonic antigen–producing human gastric carcinoma cells in vitro." *Cancer Research*, 1996, 56(6):1341–1345. Biosciences Information Service, Philadelphia, PA. DATABASE Biosis Online! (XP002206230).
Kenneth Drazan et al., "Transduction of hepatic allografts achieves local levels of viral IL–10 which suppress alloreactivity in vitro." *J. of Surgical Research*, 1995, 59(1):219–223. Biosciences Information Service, Philadelphia, PA. DATABASE Biosis Online! (XP002206231).
Lamers et al., Phagocytosis and degradation of DNA–anti–DNA complexes by human phagocytes. I. Assay conditions, quantitative aspects and differences between human blood monocytes and neutrophils. *European J. of Immunology*, 1981, 11(10):757–764. Database Medline (XP002206232).
Benoit et al., "Studies on the potential of microparticles entrapping pDNA–poly(aminoacids) complexes as vaccine delivery systems." *J. of Drug Targeting*, 2001, 9(4):253–266. Database Medline (XP002206233).
E. Scheicher et al., "Uptake of Microparticle–Adsorbed Protein Antigen by Bone Marrow–Derives Dendritic Cells Results in Up–Regulation of Interleukin–1Alpha and Interleukin–12 P40/P35 and Triggers Prolonged, Efficient Antigen Presentation." *European J. of Immunology*, Weinheim, DE.

* cited by examiner

*Primary Examiner*—Gerry Leffers
*Assistant Examiner*—Maria Marvich
(74) *Attorney, Agent, or Firm*—Foley & Lardner LLP (57) ABSTRACT

The inventive vector specifically directs entry into a cell of monocytic origin. The vector is composed of a nucleic acid component, a lysosome evading component and a particle that can be phagocytized. The vector itself, or cells pretreated with the vector, are useful in all gene medicine applications. Because it is specific for monocytic cells, the inventive vector is particularly suited to vaccine applications. Due to the ability of monocytic cells to target tumors, the inventive vector also is suitable for use in anti-tumor applications, including conventional gene therapy.

23 Claims, 2 Drawing Sheets

MONOCYTE-SPECIFIC PARTICULATE DELIVERY VEHICLE

BACKGROUND OF THE INVENTION

Gene-based medicine involves directly delivering a therapeutic or prophylactic gene product encoded in a nucleic acid molecule. The normal cellular transcription and translation machinery is utilized to manufacture the gene product in situ, where it is needed. When designed to integrate into the patient's genetic complement, in principle, genetic defects are curable. Moreover, when used to deliver prophylactic agents, like antigens in a vaccine regimen, quantitatively and qualitatively superior immune responses are possible.

Heretofore, however, gene-based medicine has suffered from deficiencies in delivery systems. While synthetic systems (e.g., liposome-based) and so called "naked-DNA" systems are available, they are notoriously inefficient. Thus, the delivery vehicles of choice are modified viruses. These too suffer from deficiencies, however. These deficiencies include limiting immune responses and manufacturing problems associated with obtaining infective virus.

Biolistic systems also are available. These typically entail coating metal beads with nucleic acids and delivering them with a "gene gun." The gene gun physically shoots the DNA into whatever cells can be brought into its sights. The biolistic approach, however, is non-specific. It, thus, is sub-optimal in therapeutic and prophylactic methods where specific delivery is sought. For instance, in cancer treatment methods, it is desirable to deliver the gene product only to the cancer cell, or to immediately surrounding cells.

For vaccine applications, the product desirably is specifically delivered to the best antigen presenting cells. Conventional delivery, however, is insufficient in this regard. In fact, it is believed that most of the antigen presentation in current genetic vaccine methods is accomplished via muscle cells which can present antigen, but are far less efficient than the so-called "professional" antigen presenting cells of the monocyte lineage.

Monocytic cells play a central role in the immune response. They mature into the major antigen presenting cells of the body, macrophages and dendritic cells. Moreover, as tumors grow, as part of the angiogenic process, they produce macrophage attracting factor (MAF), which draws monocytic cells to the tumor. Thus, monocytic cells, if specifically targeted, could be used either to deliver therapeutic gene products to tumor cells or to generate a therapeutic or prophylactic immune response via their superior antigen presenting properties.

Monocytic cells normally patrol the body in search of foreign, non-self antigens, typically bacteria. The monocytic cells phagocytize the bacteria, which are then digested to smaller antigenic portions in the lysosome. The resultant bacterial antigens are cycled back to the surface for presentation to the humoral and cellular arms of the immune system.

Accordingly, there is a need in the art for more specific delivery systems for gene-based drugs. A suitable delivery system would have greater specificity than biolistic methods, be more efficient than existing synthetic systems, and be less sensitive to inactivation than viral-based delivery systems.

SUMMARY OF THE INVENTION

It is an object of the invention to provide a composition for directed entry into a monocyte cell containing (i) nucleic acid encoding an antigen or therapeutic protein (ii) a lysosome evading component and (iii) a particle that can be phagocytized. In different embodiments, the nucleic acid may be DNA or RNA. In some embodiments, the nucleic acid may be encoded in an expression vector which may contain a nuclear promoter, such as CMV promoter. In other embodiments, the nucleic acid may be encoded in a cytoplasmic vector, such as a T7 vector system. In different embodiments, the lysosome/phagasome evading component may be a virus, a part of a virus, or a protein. The virus may be adenovirus and the protein may be adenovirus penton protein. In one embodiment, the present invention provides a composition for directed entry into a monocyte cell involving a recombinant non-replicative form of a virus capable of lysosome disruption, wherein the virus is adenovirus and contains nucleic acid encoding an antigen or therapeutic gene. In some embodiments, the composition may further contain a nucleic acid protecting component such as protamine, polyarginine, polylysine, histone, histone-like proteins, synthetic polycationic polymers or core protein of a retrovirus with the appropriate packaging sequence included in the RNA sequence. The components may be attached to the particle by any means which allows for attachment. In some embodiments, the nucleic acid and the lysosome evading component are attached to the particle by antibody attachment. In other embodiments, the nucleic acid and the lysosome evading component are attached to the particle by interaction between avidin and biotin. In other embodiments, the nucleic acid serves as a multiple binding vehicle. The present invention also provides a method for preparing the above described composition.

An object of the invention is to provide a method for directed delivery of a biological material into a monocyte cell involving contacting the above described composition with a monocytic cell, such as a dendritic cell or a macrophage. The present invention provides a gene therapy method involving administering the above described composition to a person in need thereof wherein the nucleic acid encodes a therapeutic protein, such as an anti-tumor protein. The present invention provides a method for gene vaccination involving administering the above described composition to a person in need thereof wherein the nucleic acid encodes an antigen, such as allergens, viral antigens, bacterial antigens or antigens derived from parasites. The present invention also provides a method for cancer treatment involving administering the above described composition to a person in need thereof wherein the nucleic acid is an anti-tumor gene, such as an anti-angiogenic factor, an immunomodulator or an anti-inflammatory factor. In the above described methods, the composition may be administered intravenously or subcutaneously.

BRIEF DESCRIPTION OF THE DRAWINGS

FIG. 2 is a photograph of human peripheral blood monocytes that have been treated with AD-GFP-beads and cultured in RPMI 1640, 10% FBS, 100 U/ml IL4 and 800 U/ml GMCSF for (A) 7 days, (B) 4 days and (C) 1 day. Engulfment of the AD-GFP-beads does not effect the cells' maturation to dendritic cells, as evidence by the cells' jagged finger-like edges which are characteristic of dendritic cells.

DETAILED DESCRIPTION OF THE INVENTION

Introduction

Figure 1:
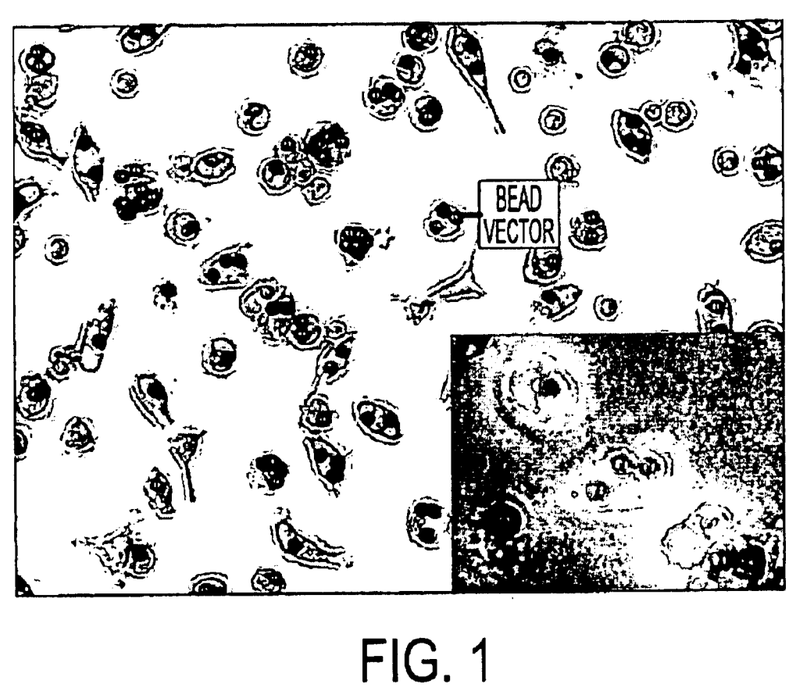
FIG. 1 is a photograph of cultured murine monocytic cells that have been treated
Figure 2A:
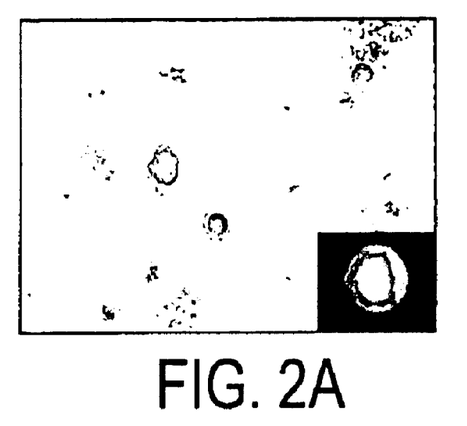
Figure 2B:
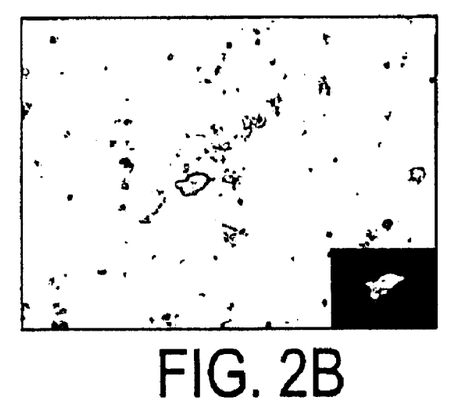
Figure 2C:
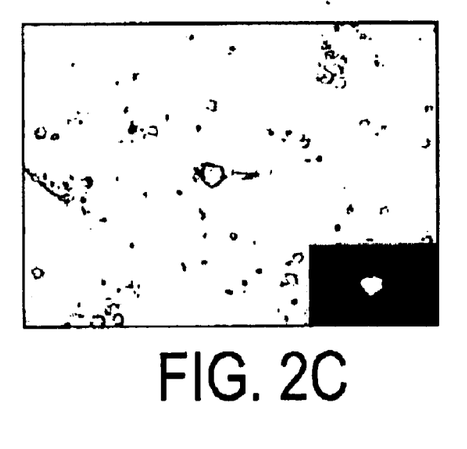

The present invention provides a solid matrix-based composition for directed entry into a monocyte cell (hereafter a "bead vector"). A basic bead vector according to the present invention is generally composed of a nucleic acid component, a lysosome evading component and a particle that can be phagocytized by monocytic cells. The bead vector is highly specific for phagocytic cells like monocyte cells, including dendritic cells and macrophages. This high selectivity for monocyte cells renders the bead vector extremely useful for gene medicine methods, requiring introduction and expression of genes into cells of the monocyte lineage, such as gene vaccination, gene therapy and cancer treatment.

Monocytes are phagocytic immune cells that ingest and present large antigens such as bacteria. The present invention takes advantage of this property in that the vectors are provided on a substrate that "looks" like a bacterium. Thus, it is believed that the size of the bead vector particle contributes to the high specificity of the bead vector for monocyte cells. A preferred size for the bead vector particle is one that approximates the size of the bacterial antigens that monocyte cells typically ingest. Generally, the vector particle will be about 0.5 to about 2.5 microns, but more preferably is about 0.5 to about 1 micron. From the perspective of uptake, the smaller end of the ranges is preferred, since they more closely approximate the size of a bacterium. On the other hand, for manufacturing purposes, slightly larger beads are preferred, because they are less likely to stick together, and so washing free from bound components is easier with the larger beads.

Of course, the bead vector is not limited by shape or material. In su the bead vector particle can be of any shape, size or material that allows the bead vector to be phagocytized by monocytic cells. Due to manufacturing convenience, a preferred matrix structure has a ferro-magnetic center covered by a polymer coat. Preferred ferro-magnetic particles are Dynabeads™ (Dynal Biotech). Dynabeads™ are monodisposed polystyrene microspheres that are available in different sizes and are coated with various material. Other preferred ferro-magnetic particles are micro-beads. Such beads are preferred because magnetic separation can be employed to separate free from bead-bound components during processing.

Nucleic Acid Component

The basic bead vector particle of the present invention generally has attached to it a nucleic acid component. The nucleic acid component typically encodes a therapeutic or antigenic nucleic acid or protein. The nucleic acid component is composed of DNA, RNA or both DNA and RNA. This component typically contains the signals necessary for translation and/or transcription (i.e., it can ultimately encode a protein or an RNA product).

The artisan immediately will comprehend the large number of therapeutic proteins that can be employed in the instant vector system. Typically, they will be anti-tumor proteins. While therapeutic proteins can be rather non-specific, since they will be localized predominantly in the immediate vicinity of a tumor, they preferably are tumor-specific. Examples of suitable therapeutic proteins include anti-angiogenic factors and interleukins.

Exemplary antigens useful in vaccine applications include allergens, viral antigens, bacterial antigens and antigens derived from parasites.

Preferred antigens include tumor associated antigens, with which the artisan will be familiar (e.g., carcinoembryonic antigen, prostate-specific membrane antigen, melanoma antigen, adenocarcinoma antigen, leukemia antigen, lymphoma antigen, sarcoma antigen, MAGE-1, MAGE-2, MART-1, Melan-A, p53, gp100, antigen associated with colonic carcinoma, antigen associated with breast carcinoma, Muc1, Trp-2, telomerase, PSA and antigen associated with renal carcinoma. Viral antigens also are preferred. Suitable viral antigens include HIV, EBV and Herpesvirus. In one embodiment, the nucleic acid encodes a linear gp41 epitope insertion (LLELDKWASL), which has been identified as a useful construct for improving HIV-1 Env immunogenicity (Liang, et al., *Vaccine*, 16; 17(22): 2862–72, July 1999).

The nucleic acid component beneficially is encoded in an expression vector, which is capable of expressing the RNA and/or protein products of the nucleic acid component. The vector typically further comprises regulatory sequences, including for example, a promoter, operably linked to the coding sequence. The vector may further comprise a selectable marker sequence, for instance for propagation in in vitro bacterial or cell culture systems. Preferred expression vectors comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 or cytomegalovirus (CMV) viral genome, for example, SV40 origin, early promoter, enhancer, splice, and polyadenylation sites may be used to provide the required nontranscribed genetic elements.

Specific initiation signals may also be required for efficient translation of inserted target gene coding sequences. These signals include the ATG initiation codon and adjacent sequences. In cases where a nucleic acid component includes its own initiation codon and adjacent sequences are inserted into the appropriate expression vector, no additional translation control signals may be needed. However, in cases where only a portion of an open reading frame (ORF) is used, exogenous translational control signals, including, perhaps, the ATG initiation codon, must be provided. Furthermore, the initiation codon must be in phase with the reading frame of the desired coding sequence to ensure translation of the entire target.

These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544 (1987)). Some appropriate expression vectors are described by Sambrook, et al., in *Molecular Cloning: A Laboratory Manual*, Second Edition, Cold Spring Harbor, N.Y. (1989), the disclosure of which is hereby incorporated by reference. If desired, to enhance expression and facilitate proper protein folding, the codon context and codon pairing of the sequence may be optimized, as explained by Hatfield et al., U.S. Pat. No. 5,082,767.

Promoters include CMV immediate early, HSV thymidine kinase, early and late SV40, LTRs from retrovirus, and mouse metallothionein-I. A preferred promoter is CMV. Exemplary vectors include pWLneo, pSV2cat, pOG44, pXT1, pSG (Stratagene) pSVK3, pBPV, pMSG, and pSVL (Pharmacia). Selectable markers include CAT (chloramphenicol transferase). Preferred vectors also include cytoplasmic vectors, like the T7 vector system. See Wagner et al., U.S. Pat. No. 5,591,601 (Jan. 7, 1997).

Lysosome Evading Component

In addition to the nucleic acid component, the basic bead vector particle of the present invention also generally has attached to it a lysosome evading component. The role of the lysosome evading component with respect to the bead vector is to assist the vector in escaping the harsh environment of the lysosome. Aside from those disclosed herein, the skilled artisan will be aware of numerous examples of such molecules.

When a monocytic cell ingests a large antigen, a phagocytic vesicle (phagasome) is formed which engulfs the antigen. Next, a specialized lysosome contained in the monocyte cell fuses with the newly formed phagosome. Upon fusion, the phagocytized large antigen is exposed to several highly reactive molecules as well as a concentrated mixture of lysosomal hydrolases. These highly reactive molecules and lysosomal hydrolases digest the contents of the phagosome. Therefore, by attaching a lysosome evading component to the particle, the nucleic acid that is also attached to the particle escapes digestion by the materials in the lysosome and enters the cytoplasm of the monocyte intact. Prior systems failed to recognize the importance of this important feature and, thus, obtained much lower levels of expression than the present invention. See Falo et al., WO 97/11605 (1997). It should be noted that the term "lysosome evading component" encompasses the fused lysosome/phagosome described above.

The lysosome evading component is any component that is capable of evading or disrupting the lysosome. For example, the lysosome evading component can include proteins, carbohydrates, lipids, fatty acids, biomimetic polymers, microorganisms and combinations thereof. It is noted that the term "protein" encompasses a polymeric molecule comprising any number of amino acids. Therefore, a person of ordinary skill in the art would know that "protein" encompasses a peptide, which is understood generally to be a "short" protein. Preferred lysosome evading components include proteins, viruses or parts of viruses. The adenovirus penton protein, for example, is a well known complex that enables the virus to evade/disrupt the lysosome/phagosome. Thus, either the intact adenovirus or the isolated penton protein, or a portion thereof (see, for example, Bal et al., Eur J Biochem 267:6074–81 (2000)), can be utilized as the lysosome evading component. Fusogenic peptides derived from N-terminal sequences of the influenza virus hemagglutinin subunit HA-2 may also be used as the lysosome evading component (Wagner, et al., *Proc. Natl. Acad. Sci. USA*, 89:7934–7938, 1992).

Other preferred lysosome evading components include biomimetic polymers such as Poly (2-propyl acrylic acid) (PPAAc) which has been shown to enhance cell transfection efficiency due to enhancement of the endosomal release of a conjugate containing a plasmid of interest (see Lackey et al., *Abstracts of Scientific Presentations: The Third Annual Meeting of the American Society of Gene Therapy*, Abstract No. 33, May 31, 2000–Jun. 4, 2000, Denver, Colo.) Examples of other lysosome evading components envisioned by the present invention are discussed by Stayton, et al. *J. Control Release*, 1;65(1–2):203–20, 2000.

Nucleic Acid Protection Component

In addition to the components described above which are generally attached to the basic bead vector particle, either directly or via attachment to one another (e.g., a recombinant adenovirus encoding a nucleic acid), other components may also be attached to the particle or to a component that is attached to the particle. For example, a DNA protecting component may optionally be added to the basic bead vector described above, especially where the nucleic acid component is not associated with a virus or a portion thereof. Generally, the DNA protecting component will not be attached directly to the bead. The nucleic acid protecting component includes any component that can protect bead-bound DNA or RNA from digestion during brief exposure to lytic enzymes prior to or during lysosome disruption. Preferred nucleic acid protecting components include protamine, polyarginine, polylysine, histone, histone-like proteins, synthetic polycationic polymers and core protein of a retrovirus with the appropriate packaging sequence included in the RNA sequence.

In one embodiment of the present invention, the bead vector comprises (1) a recombinant, optionally non-replicative and/or non-infective, form of a virus which contains a nucleic acid encoding an antigen or therapeutic gene and (2) a particle that can be phagocytized. The virus may be an RNA virus, like a retrovirus, or a DNA virus, like an adenovirus. In this embodiment, the virus itself preferably is capable of lysosome disruption. In other words, the nucleic acid and lysosome evading components are both integral parts of the virus. Alternatively, the virus may not be capable of lysosome disruption. In such a case, of course, a separate lysosome evading component should be added. Preferred viruses include HIV, adenovirus, Sindbis virus, and hybrid and recombinant versions thereof. A particularly preferred virus is an HIV-adenovirus hybrid, which is essentially a recombinant adenovirus that has been engineered to express HIV antigens. Viruses can be attached to the beads directly, using conventional methods. See Hammond et al., *Virology* 254:37–49 (1999).

Since viral infection is not essential in the present invention for the nucleotide component to reach the cytoplasm of the monocyte cell, the virus can also be replication/infection deficient. One method for producing a replication/infection deficient adenovirus envisioned by the instant invention is altering the virus fiber protein. For example, a virus in which the fiber protein is engineered by specific mutations to allow the fiber protein to bind to an antibody but not to its cognate cellular receptor can be used in the instant invention.

Another method for producing a replication/infection deficient virus envisioned by the present invention is intentionally causing denaturation of the viral component responsible for infectivity. In the case of adenovirus, for example, the fiber protein could be disrupted during the preparation of the virus; for HIV it might be the envelope (env) protein. A method for producing a replication/infection deficient retrovirus envisioned by the present invention entails removing the outer membranes of the retrovirus so that only the retrovirus core particle remains. If a replication/infection deficient virus prepared as described above is attached to the bead vector particle, a RNA protecting component, as described above, may also be attached to the particle.

In some therapeutic embodiments, it is beneficial for the vector to stably integrate into the target cell chromosome. For example, one mode for achieving stable integration is through the use of an adenovirus hybrid. Such an adenovirus hybrid involves, for example, an adenoviral vector carrying retrovirus 5' and 3' long terminal repeat (LTR) sequences flanking the DNA component encoding a therapeutic or antigenic nucleic acid or protein and a retrovirus integrase gene (see Zheng, et al. *Nature Biotechnology*, 18:176–180, 2000). In other embodiments, transient expression is preferred and cytoplasmic viruses, like Sindbis virus, can be employed. In such cases, where no lysosome evading component is naturally present on the virus, one is added. In the case of Sindbis or other such viruses, it can be engineered to express all or part of the adenovirus penton protein for this purpose, for example.

Methods for Attaching the Components to the Particle

Attachment of the components discussed above to the bead vector particle is accomplished by any means. As set out above, the various "components" include a nucleic acid, a lysosome evading component, which may both be present in a virus. Preferred methods for attachment include antibody attachment, biotin-avidin interaction and chemical crosslinking. Bead vector particles may be prepared with chemically attached antibodies, avidin or other selective attachment sites.

Antibody attachment can occur via any antibody interaction. Antibodies include, but are not limited to polyclonal antibodies, monoclonal antibodies (mAbs), humanized or chimeric antibodies, single chain antibodies including single chain Fv (scFv) fragments, Fab fragments, $F(ab')_2$ fragments, fragments produced by a Fab expression library, anti-idiotypic (anti-Id) antibodies, epitope-binding fragments, and humanized forms of any of the above.

In general, techniques for preparing polyclonal and monoclonal antibodies as well as hybridomas capable of producing the desired antibody are well known in the art (Campbell, A. M., *Monoclonal Antibody Technology: Laboratory Techniques in Biochemistry and Molecular Biology*, Elsevier Science Publishers, Amsterdam, The Netherlands (1984); St. Groth et al., *J. Immunol. Methods* 35:1–21 (1980); Kohler and Milstein, *Nature* 256:495–497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96).

One example of antibody attachment encompassed by the present invention involves a single antibody which is chemically affixed to the bead vector particle. The antibody is specific to the component to be attached to the particle. Alternatively, two antibodies can be used. In this case, one antibody, attached to the bead, is specific for a second antibody. The second antibody is specific to the component to be attached to the bead. Thus, the component-specific antibody binds the component, and that antibody, in turn, is bound by the bead-bound antibody. For instance, a goat- or rabbit-anti-mouse antibody may be bound to the bead and a mouse monoclonal antibody used to bind the specific component.

In other example of antibody attachment, protein A, or any similar molecule with an affinity for antibodies, is employed. In this example, the beads are coated with protein A which binds to an antibody, which in turn is bound to the component being attached to the bead.

Attachment via biotin-avidin interaction may be accomplished, for instance, by attaching avidin to the bead vector particle and attaching biotin to the component to be attached. Chemical crosslinking may be accomplished by conventional means known to the artisan.

Another attachment mechanism involves the nucleic acid serving as a multiple binding vehicle. Synthetic gripper protein nucleic acid (PNA) oligonucleotides are designed to specifically bind to different nucleic acid sequences. PNA is a polynucleic acid analog with a peptide backbone rather than a deoxyribosephosphate backbone. These can be attached directly to the bead or derivatized for convenient attachment, thereby providing a sequence-specific means of attaching nucleic acid. Each gripper oligonucleotide can be derivatized or attached to different ligands or molecules and designed to bind different nucleic acid sequences. It is believed that the PNA interacts with the DNA via Hoogsteen base pairing interactions and that a stable PNA-DNA-PNA triplex clamp is formed (Zelphati, et al. *BioTechniques*, 28:304–316, 2000).

Thus, in one embodiment, one gripper is employed to bind the nucleic acid component to the bead and another is used to bind the lysosome evading component to the nucleic acid component. Many such iterations are possible. For example, a "gripper" comprising biotin can be sequence specifically bound at one site to the nucleic acid. Attachment to a particle coated with avidin occurs via biotin-avidin interaction. At another site on the nucleic acid, another "gripper" with a lysosome/phagasome evading component can be sequence specifically bound. Optionally, a "gripper" with a DNA protecting component can be sequence specifically bound to the nucleic acid at yet another site. Exemplary gripper oligonucleotides have been previously described.

In the case of attaching viruses to bead, this can also be accomplished by engineering the virus to express certain proteins on its surface. For instance, the HIV env protein might be replaced with the adenovirus penton protein, or a portion thereof. The recombinant virus then could be attached via an anti-penton antibody, with attachment to the bead mediated, for example, by another antibody or protein A. In this embodiment, the penton protein also would serve as a lysosome evading component.

Formulation

The bead vector may be formulated for parenteral administration by, for example, intravenous, intramuscular or subcutaneous injection. Formulations for injection may be presented in unit dosage form, e.g., in ampules or in multidose containers, optionally with an added preservative. The compositions may take such forms as suspensions, solutions or emulsions in oily or aqueous vehicles, and may contain formulatory agents such as suspending, stabilizing and/or dispersing agents. The bead vector may also be formulated using a pharmaceutically acceptable excipient. Such excipients are well known in the art, but typically will be a physiologically tolerable aqueous solution. Physiologically tolerable solutions are those which are essentially non-toxic. Preferred excipients will either be inert or enhancing.

Therapeutic Methods

The inventive bead vector is highly selective for cells like monocyte cells. It is, therefore, useful for any application involving selectively introducing a nucleic acid component into a monocyte cell, including gene vaccination, cancer treatment and gene therapy. Typical methods entail contacting a monocytic cell with a bead vector.

The bead vector can be contacted with monocyte cells either in vivo or in vitro. Hence, both in vivo and ex vivo methods are contemplated. As for in vivo methods, the bead vector generally is administered pareterally, usually intravenously, intramuscularly, subcutaneously or intradermally. It may be administered, e.g., by bolus injection or continuous infusion. In ex vivo methods, monocytic cells are contacted outside the body and the contacted cells are then administered to the patient. The cells also are administered parenterally, typically via infusion.

In the field of vaccination, monocyte cells, including dendritic cells and macrophages, are considered "professional" antigen presenting cells (APCs) and, thus, are the ideal site for expression of a genetic vaccine. It is well known that expression of an antigen within an APC is vastly more effective in generating a strong cellular immune response than expression of this same antigen within any other cell type. Therefore, the ability of the bead vector of the instant invention to direct the expression of a vaccinating antigen to "professional" antigen presenting cells (monocyte cells) dramatically enhances the efficacy of a genetic vaccine.

The present invention offers a substantial improvement over the prior art vaccines because the bead vector may be injected directly into the patient, yet it is able to directly deliver the antigen to the body's best antigen presenting cells, cells of monocytic origin, like macrophages and dendritic cells. Prior methods that targeted these cells rely principally on isolated a patient's monocytic cells and manipulating them in vitro and then returning the cells to the patient. While such a scenario is contemplated as within the invention, a substantial improvement is that this step need not be done. In other words, the bead vector may be administered just like a conventional vaccine, which substantially reduces cost because of the lower level of skill required. Moreover, it is contemplated that altering the route of administration can alter the monocytic cells targeted. For example, in the case of intravenous injection, macrophages should be targeted, and in the case of subcutaneous injection, dendritic cells should be the target.

Typical methods for gene vaccination involving the present inventive bead vector include administering, generally subcutaneously or intravenously, to a patient a bead vector which contains containing nucleic acid encoding an antigen. Alternatively, monocytic cells may be contacted with the vector ex vivo and then the cells themselves parenterally administered to the patient. In addition, this ex vivo method may be modified by isolated T lymphocytes, using the contacted monocytic cells to ex vivo generate antigen-specific cytotoxic T cells, which then may be administered to the patient. The skilled artisan will be familiar with such strategies.

In addition to improved vaccination strategies, targeting gene expression to the monocytic cell lineage using the bead vector of the instant invention is effective for cancer treatment. One type of cancer treatment encompassed by the instant invention involves targeting a therapeutic gene to a tumor. It is known that as tumors, primary tumors and metastases alike, grow beyond a few millimeters in diameter and become deficient in oxygen, they secrete signal proteins to elicit several required events for the tumor's survival. These events include the secretion of signals which induce angiogenesis. As a part of the mechanism of angiogenic induction, hypoxic tumors secrete a signaling chemokine protein with the function of attracting monocytes to the tumor. Monocytes thus attracted to the sites of growing tumors then become macrophages and assist in the induction of tumor angiogenesis. Therefore, an effective method of therapeutic gene tumor targeting involves administering an effective amount of a bead vector containing an anti-tumor gene to a cancer patient, either directly or via an ex vivo contacted cell. The monocyte cells containing the phagocytized bead vector should be attracted to the sites of tumor development and deliver the therapeutic tumor gene selectively to the tumor.

In one embodiment, the anti-tumor gene is an anti-angiogenic factor, like endostatin or angiostatin. Such a treatment is envisioned to be highly effective because it utilizes the monocytes, which normally deliver pro-angiogenic factors to the tumor, as a delivery vehicle for anti-antiogenic factors.

In another embodiment, the anti-tumor gene may be an immunomodulator or an anti-inflammatory factor. Immunomodulators like IL-2 and IL-12 are envisioned. Moreover, anti-inflammatory factors not only would be useful in treating tumors, but also in treating chronic inflammatory disorders like arthritis. The anti-inflammatory effects of the invention, like the anti-tumor effects, rely on the ability of monocytic cells to home to the particular tissue. It is well known that monocytes are attracted to the cites of inflammatory response, like those in arthritis. Other exemplary immunomodulators and anti-inflammatories include GM-CSF and soluble TNF-alpha receptor.

Another use of the bead vector encompassed by the instant invention is for conventional gene therapy. Typical methods for gene therapy involving the present inventive bead vector include administering to a patient a bead vector which contains a nucleic acid encoding a therapeutic gene, or a cell containing that vector, to a patient. The nucleic acid encodes any therapeutic gene.

The following non-limiting examples are given by way of illustration only and are not to be considered limitations of this invention. There are many apparent variations within the scope of this invention.

EXAMPLE 1

This example demonstrates the construction of a typical bead vector.

An exemplary bead vector comprises adenovirus which has been engineered to contain the gene encoding Green Fluorescent Protein (GFP) attached to a Dynabead (Ad-GFP-bead). To make the AD-GFP-bead, first, Dynabeads (Dynal, prod. No. 115.19) were thoroughly resuspended and the desired amount of beads was transferred to a tube suitable for the magnetic device. The beads were washed three times with 1–2 ml buffer (RPMI with 1% FCS) with magnetic assistance. The beads were resuspended back into the original buffer volume. Next, in order to coat the beads with with anti-adenovirus fiber protein antibody AB-4 (Neomarker, cat. No. MS-1027), 2 micrograms mouse IgG were added per $10^7$ beads. After rotating the bead/antibody mixture for 30 minutes at room temperature, the beads were washed 3 times with buffer (PBS plus 1% BSA) using magnetic assistance. The coated beads were then resuspended back into the original volume of buffer (PBS plus 1% BSA). In order to bind the adenovirus particles (Quantum, Ad5.CMV5-GFP) to the beads, $0.5 \times 10^8$ viral particles/$10^7$ were added. After rotating the mixture for 30 minutes at 4° C., the beads were washed 3 to 4 times with buffer (PBS plus 1% BSA) using magnetic assistance. Finally, the beads were resuspended in an appropriate volume of buffer (PBS plus 1% BSA, PH 7.4) for in vitro or in vivo use.

EXAMPLE 2

This example demonstrates that monocytic cells specifically take up the inventive bead vector in vitro. In this experiment, the Ad-GFP vector of Example 1 was incubated with a mixed culture containing monocytes. Examination by microscopy revealed high levels of GFP expression only in monocytic cells.

In this example, 50–100 ml of blood was obtained from a human donor and placed in sodium heparin tubes. The blood was diluted 1:1 with 1×PBS. 8 ml of the diluted blood was layered over 4 mls of room temperature Ficoll-Paque Plus in a 15 ml centrifuge tube. The tubes were centrifuged at 400 g at room temperature for 30 minutes. The PBMC layer was carefully removed from the Ficoll gradient using a pasteur pipet and put into a clean 15 or 50 ml centrifuge tube. 4 volumes of 1×PBS were added to the tubes and the tubes were inverted to mix. The tubes were centrifuged at 100 g at room temperature for 10 minutes. 10 mls of 1×PBS was added and the tubes were inverted to mix the cells. The tubes were centrifuged at 100 g at room temperature for 10 minutes. An AKC lysis was performed for 5 minutes at room temperature and the cells were pelleted and washed with 1×PBS. The PBMC's were suspended in 5 mls of complete dendritic cell medium (RPMI1640+10% FBS+800 U/ml GM-CSF+1000 U/ml IL-4). The PBMC cells were then plated into 6 well plates. Next, AD-GFP-beads prepared as described in Example 1 were added into the culture at different cell to bead ratios. The plate was swirled to make the vectors evenly distributed in the culture. The expression of GFP was monitored under a fluorescence microscope every day. The culture medium was refreshed every other day. The differentiation of PBMC into dendritic cells was monitored by the observation of the unique morphology of dendritic cells.

Mice peritoneal cavity macrophages were prepared by injecting 3 mls of 1×PBS into the peritoneal cavity. After gentle message, the injected solution was recovered and the cells were put into a culture plate. After one hour incubation, the unattached cells were removed and the attached cells were retained for and cultured in DMEM plus 10% FBS.). The cells were then plated into 6 well plates. Next, AD-GFP-beads prepared as described in Example 1 were added into the culture at different cell to bead ratios. The plate was swirled to make the vectors evenly distributed in the culture. The expression of GFP was monitored under a fluorescence microscope every day. The culture medium was refreshed every other day. The differentiation of PBMC into dendritic cells was monitored by the observation of the unique morphology of dendritic cells. The plate was swirled to make the vectors evenly distributed in the culture.

EXAMPLE 3

This example demonstrates that monocytic cells specifically take up the inventive bead vector in vivo and that the cells that took up the vector migrate to the lymph nodes which mimics the normal immune response. This is proof of principle that the monocytic cells, once they phagocytize the vector, actively migrate to the lymphatic system, where the immune response is generated. The vector of Example 1 was injected IP into mice at the midline. After 24 hours, the axillary lymph nodes were removed and examined microscopically. Monocytes expressing high levels of GFP were observed.

EXAMPLE 4

This example demonstrates that the inventive bead vector elicits a specific immune response. In this example, the inventive bead vector is used for gene vaccination. An exceptionally strong immune response resulting from the bead vaccination is observed. Two C57B16 adult male mice were vaccinated by a subcutaneous injection of $5 \times 10^8$ 2.5 micron microbeads coated with AD5,CMV-GFP in 250 $\mu$l on day 1, day 7, and day 14. On day 21 these mice were sacrificed, their spleens removed and lymphocytes prepared from these spleens. These lymphocytes and lymphocytes from non-immunized C57B16 mice were then co-cultured for 7 days in separate wells of a micro-titer plate with B16 cells (C57B16 background) previously transfected with the CMV-GFP gene and expressing GFP at a ratio of approximately 1:1. The cells from these co-cultures were then used at a ratio of effector cells (co-cultured lymphocytes) to target cells of 1000:1 in a standard CTL assay.

For the CTL assay, additional B16 cells expressing GFP were first incubated in radio labeled sodium chromate ($^{51}$Cr), washed and used as target cells. These target cells were then incubated for 4 hours with the stimulated lymphocytes from the two vaccinated mice (Experimental Group), two non-immunized C57B16 mice (Control Group), RPMI medium alone (Spontaneous Release Group) and with 2% Triton×100 (Maximum Release Group). The radioactivity resulting from the release of internal $^{51}$Cr (a measure of cell lysis) from the cells in each of these incubation cultures was determined by counting the radioactivity in aliquots of the supernatant from each of these incubation cultures after mild centrifugation. The averaged counts from the Maximum release group was 5160.5 CPM, from the spontaneous release group was 2941.5 CPM, from the control group was 3015.5 CPM and from the experimental group was 5175.5 CPM. These results clearly show that the bead-vaccinated mice developed a strong cytotoxic T-lymphocyte (CTL) response to their vaccination, carrying out the lysis of 100% of the target cells in this CTL assay.

When this experiment was repeated exactly as above except that the lymphocytes used in the final CTL assay were taken directly from the vaccinated mouse spleens without the week of co-culture with GFP expressing cells, the CTL assay showed that these unstimulated lymphocytes at a ratio of effector cells to target cells of only 100:1 caused the lysis of 34% of the target cells. Such CTL activity without pre-stimulation by co-culture is highly unusual and suggests an exceptionally strong immune response resulting from the bead vaccination.

EXAMPLE 5

This example demonstrates that only low levels of expression are obtained when the lysosome evading component is omitted from the system.

To make the bead vector for this example, a GeneGrip site duplex oligonucleotide from Gene Therapy System was cloned into a T7T7/T7GFP vector. Then a biotin pGeneGrip PNA label was used to label the aforementioned T7 vector to form a T7T7/T7GFPvector/pGeneGrip PNA construct. Next, Dynabeads coated with streptavidin in an appropriate ratio were contacted with the T7T7/T7vector/pGeneGrip PNA construct. After extensive washing, the beads were mixed with T7 RNA polymeraes and incubated on ice for 30 min to yield T7T7/T7vector/pGeneGrip PNA bead vectors.

Macrophage cells were prepared as described in Example 2. Next, T7T7/T7vector/pGeneGrip PNA bead vectors were added into the culture at different cell to bead ratios. The plate was swirled to make the vectors evenly distributed in the culture. The expression of GFP was monitored under a fluorescence microscope every day. The culture medium was refreshed every other day. Only a very few cells were detected that seemed to have faint GFP expression. The faint green fluorescence could be seen by eye through the microscope but was difficult or impossible to see in photomicrographs or to distinguish this expression level from the background fluorescence in these micrographs. Immunocytochemistry staining was also conducted to determine the expression level of GFP using anti-GFP antibody. The expression level of GFP was detectable but very low.

EXAMPLE 6

This example demonstrates that human monocytic cells specifically take up the inventive bead vector in vitro. After the cells are differentiated to dendritic cells, the cells continue to express high levels of GFP. Thus, the bead vector can be phagocytized by monocytic cells and this does not interfere with their maturation to dendritic cells.

In this experiment, human peripheral blood monocytes were contacted with the Ad-GFP vector of Example 1. The mixture was then cultured for 7 days in RPMI 1640, 10% FBS, 1000 U/ml IL4 and 800 U/ml GMCSF. After 7 days, 50% of the cells are expressing high levels of GFP. The differentiated cells had characteristic dendritic cell morphology.

We claim:

1. A composition for directed entry into a monocyte cell comprising (i) nucleic acid encoding a protein (ii) a lysosome evading component and (iii) a bead vector particle that can be phagocytized, wherein said lysosome evading component is a non-infectious virus or non-infectious component of a virus.

2. The composition of claim 1 wherein said nucleic acid is selected from the group consisting of DNA and RNA.

3. The composition of claim 1 wherein said nucleic acid is encoded in an expression vector.

4. The composition of claim 3 wherein said expression vector contains a nuclear promoter.

5. The composition of claim 4 wherein said promoter is a CMV promoter.

6. The composition of claim 1, wherein said virus is adenovirus.

7. The composition of claim 1 further comprising a nucleic acid protecting component.

8. The composition of claim 7 wherein said component is selected from the group consisting of protamine, polyarginine, polylysine, histone, histone-like proteins, synthetic polycationic polymers and a core particle of a retrovirus with the appropriate packaging sequence included in the RNA sequence.

9. The composition of claim 1 wherein said nucleic acid and said lysosome evading component are attached to the particle by antibody attachment.

10. The composition of claim 1 wherein said nucleic acid and said lysosome evading component are attached to the particle by interaction between avidin and biotin.

11. The composition of claim 1 further comprising a multiple binding vehicle that binds the nucleic acid.

12. The composition of claim 1 wherein said lysosome evading component is the adenovirus penton protein.

13. The composition of claim 1, wherein said non-infectious virus or non-infectious component of a virus is non-replicative.

14. The composition of claim 1, wherein said composition is a pharmaceutical composition that comprises a pharmaceutically suitable excipient.

15. The composition of claim 14, wherein said non-infectious virus or non-infectious component of a virus is non-replicative.

16. The pharmaceutical composition of claim 14, wherein said protein is an antigen.

17. The composition of claim 1, wherein said protein is an antigen.

18. A composition for directed entry into a monocyte cell comprising (i) nucleic acid encoding a protein, (ii) a lysosome evading component and (iii) a bead vector particle that can be phagocytized, wherein said lysosome evading component is a biomimetic polymer.

19. The composition of claim 18, wherein said protein is an antigen.

20. The composition of claim 18, wherein said composition is a pharmaceutical composition that comprises a pharmaceutically suitable excipient.

21. A composition for directed entry into a monocyte cell comprising (i) nucleic acid encoding a protein (ii) a lysosome evading component and (iii) a bead vector particle that can be phagocytized, wherein said lysosome evading component is a non-infectious virus.

22. A composition for directed entry into a monocyte cell comprising (i) nucleic acid encoding a protein (ii) a lysosome evading component and (iii) a bead vector particle that can be phagocytized, wherein said lysosome evading component is a non-infectious component of a virus.

23. A composition for directed entry into a monocyte cell comprising (i) nucleic acid encoding a protein (ii) a lysosome evading component and (iii) a bead vector particle that is about 0.5 to about 2.5 microns and allows the composition to be phagocytized by monocytic cells, and wherein the lysosome evading component is a non-infectious virus or non-infectious component of a virus.

* * * * *

UNITED STATES PATENT AND TRADEMARK OFFICE
CERTIFICATE OF CORRECTION

PATENT NO. : 6,875,612 B2 Page 1 of 1
DATED : April 5, 2005
INVENTOR(S) : Thomas E. Wagner and Xianzhong Yu It is certified that error appears in the above-identified patent and that said Letters Patent is hereby corrected as shown below:

<u>Title page,</u>
Item [75], Inventor, change "Xianzhang Yu" to -- Xianzhong Yu --.

Signed and Sealed this

Seventh Day of June, 2005

JON W. DUDAS
*Director of the United States Patent and Trademark Office*